United States Patent [19]

Leibinger et al.

[11] Patent Number: 5,394,457
[45] Date of Patent: Feb. 28, 1995

[54] DEVICE FOR MARKING BODY SITES FOR MEDICAL EXAMINATIONS

[75] Inventors: Karl Leibinger, Tuttlingen; Franz Leibinger, Mülheim-Stetten, both of Germany; Stephan Felber, Aldrans; Clemens Plangger, Telfs, both of Austria

[73] Assignee: Leibinger GmbH, Germany

[21] Appl. No.: 133,675

[22] Filed: Oct. 7, 1993

[30] Foreign Application Priority Data

Oct. 8, 1992 [DE] Germany .............................. 4233978

[51] Int. Cl.⁶ .............................................. A61B 19/00
[52] U.S. Cl. ...................... 378/162; 378/205; 128/653.4
[58] Field of Search ............... 378/162, 163, 164, 205, 378/170, 204; 128/653.1, 653.4, 654; 606/130; 324/309

[56] References Cited

U.S. PATENT DOCUMENTS

| 4,341,220 | 7/1982 | Perry | 378/162 X |
| 4,360,028 | 11/1982 | Barbier et al. | 378/162 X |
| 4,578,806 | 3/1986 | Grass et al. | 378/162 |
| 4,608,977 | 9/1986 | Brown | 378/162 X |
| 4,618,978 | 10/1986 | Cosman | 378/162 X |
| 4,884,566 | 12/1989 | Mountz et al. | 378/205 X |
| 4,985,019 | 1/1991 | Michelson | |
| 4,991,579 | 2/1991 | Allen | |
| 5,208,845 | 5/1993 | Gelb | 378/205 X |

FOREIGN PATENT DOCUMENTS

2212371A  7/1989  United Kingdom .

Primary Examiner—David p. Porta
Attorney, Agent, or Firm—Jones, Day, Reavis & Pogue

[57] ABSTRACT

A device for marking body sites for imaging medical examinations, such as nuclear spin resonance tomography (NMR), computed tomography (CT), roentgen ray analysis (X-ray), or positron emission tomography (PET), comprises fixtures (10) which are adapted to be fastened to the body and/or to a stereotaxic means or a mask arrangement. Markers (18) containing a substance (20) which provides sharp contrast in the generation of images are adapted to be slid selectively into those fixtures. The fixtures are made of a material which does not disturb the imaging, with at least two different imaging examination procedures.

22 Claims, 4 Drawing Sheets

DEVICE FOR MARKING BODY SITES FOR MEDICAL EXAMINATIONS

FIELD OF THE INVENTION

The instant invention relates to a device for marking locations on the body for imaging-type medical examination procedures, such as especially nuclear spin resonance tomography (NMR), computed tomography (CT), roentgen ray analysis (X-ray), or positron emission tomography (PET), comprising fixtures adapted to be fastened to the body or to a stereotaxic means and markers adapted to be fastened to the fixtures and containing a substance which provides a high degree of contrast in the imaging process.

BACKGROUND OF THE INVENTION

Highly accurate examinations of anatomical structures are required especially when stereotaxic surgery is to be performed, in other words brain surgery where a target device attached to a patient's head is used to advance a probe or electrode with millimeter precision through a small aperture drilled into the bony skull to a deep-seated brain path or nerve nucleus, while preserving adjacent sensitive structures.

To accomplish that, so-called marker systems are applied to the patient.

SUMMARY OF THE INVENTION

It is the object of the invention to provide a device for marking body sites for imaging-type medical examination procedures by means of which different examination procedures can be applied in simple manner in a way so as to complement each other.

This object is met, according to the invention, in that the fixtures of the marker system are made of a material which will not disturb the generation of the image in at least two different imaging examination procedures.

Such marker systems for frameless stereotaxis are attached to the patient. They consist of the fixtures mentioned above and of the actual markers, i.e. those elements which contain a substance that provides particularly good contrast so as to appear clearly in the image during the medical examination procedure to be undertaken. The fixtures are designed so that they can either be implanted, adhered to the surface of the body, secured to mask arrangements, or mounted on stereotaxic assemblies. The markers themselves can be mounted in exchangeable fashion on the fixtures. Each marker contains a substance which will give sharp contrast to the image in the image generation process, or essentially is made of such a substance. Imaging processes of particular interest in the present context are the nuclear spin resonance tomography (NMR), computed tomography (CT), X-ray analysis, and positron emission tomography (PET).

It is preferred according to the invention that the markers should be designed so that a video camera can take pictures of them and/or that they can be recognized through an operating microscope. The operating microscope allows positional feedback in such a way that precise locating becomes possible.

The location of a patient in space, in particular also the position of his head can be determined by means of at least three differently placed markers. If a patient is subjected to different medical examinations with different imaging techniques, of which examples were given above, both the examination and a possible surgical intervention can be improved or facilitated by applying different examining routines in supplementary manner. Once the relative position of the patient has been determined accurately (e.g. that of his or her head) for the images obtained by the various techniques, the different imaging examination procedures can be superimposed over one another, for example strictly mathematically in a computer.

Different anatomical data are obtained due to the different characteristics of the different imaging medical examination procedures. For example, good X-ray pictures can be made of cerebral blood vessels by means of digital subtraction angiography. NMR often provides good pictures of edema. CT, on the other hand, is good for presentations of bone structure and for information on density, such as required for radiation therapy.

Under strict requirements as to accuracy, which prevail above all with regard to the head, the invention makes it possible to superpose and/or compare the results obtained from various imaging processes.

The solution according to the invention, as outlined above, makes it possible to use the markers according to the invention for sharp-contrast presentations in different imaging processes without having to change their place. The fixtures employed for the markers are characterized by having a configuration and consisting of a material such that they do not disturb the image of the markers or of the anatomical structures to any degree worth mentioning.

The markers, moreover, are designed so that they always comprise a suitable material as regards their sheath and the contrast medium proper for different imaging processes. It is easy to replace such markers, as desired, in correspondence with the respective imaging process, while the fixtures remain the same.

The fixtures, markers, and contrast media each consist of material which is admitted for the particular purpose in question. Besides, it should be noted that it is only the fixtures which come into direct contact with the patient.

In the case of so-called projection images, such as X-ray pictures, two exposures taken from different directions are sufficient to permit the locus determination to be made for any desired point.

In the case of so-called sectional images, images including the markers so that these are visible, are sufficient for determining a site in space.

For stereotaxially guided interventions, additional images are required to transmit predetermined target points to the stereotaxic system, such additional images showing both the markers and the position of the stereotaxic system. This may be accomplished by different imaging techniques. In this manner target points and surgical access paths can be chosen and transferred to the patient, while, at the same time, a stereotaxic system is used in one of the imaging processes or an operating microscope which permits a bearing to be taken of the markers and to determine their position in space.

BRIEF DESCRIPTION OF THE DRAWING

Several embodiments of fixtures and their associated markers will be specified in greater detail below.

In the drawings.

DESCRIPTION OF THE PREFERRED EMBODIMENTS

Figure 1:
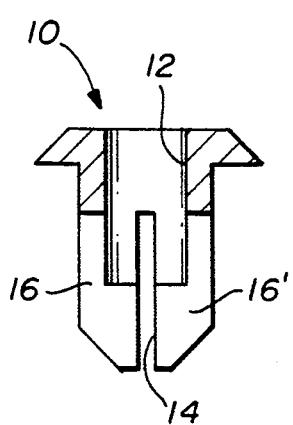
FIG. 1 shows a fixture for fastening markers.

FIG. 1 presents a fixture adapted to be fastened to a mask arrangement which is known per se. The fixture 10 according to FIG. 1 is made of plastics and formed with a recess 12 into which a marker can be slid, which will be described in greater detail below. The plastic fixture includes two spreader wings 16, 16' between which a slot 14 is left open.

Figure 2:
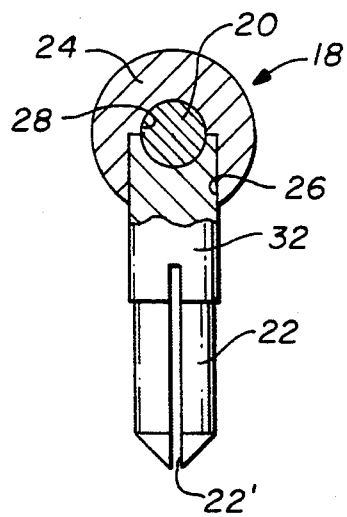
FIG. 2 shows a first embodiment of a marker which can be employed together with a fixture as shown in FIG. 1.
Figure 3:
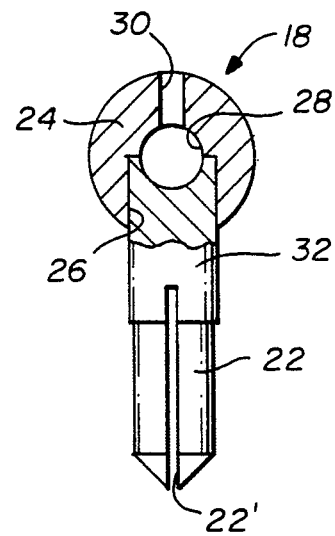
FIG. 3 shows a second embodiment of a marker which likewise can be employed together with a fixture according to FIG. 1.

FIGS. 2 and 3 each illustrate a marker 18 which can be used together with a fixture 10 according to FIG. 1.

A marker 18 contains a contrasty substance 20 for the particular medical imaging examination procedure in question. Suitable materials are known to those skilled in the art, and examples thereof will be given as the description proceeds.

The marker 18 includes a limb 22 adapted to be fitted snugly and with clamping effect in the recess 12 of the fixture 10. To accomplish that, the limb 22 is formed with a slit 22' which will help establish the clamping effect.

The limb 22 passes over into a head 24 in which a cavity 28 is provided to receive the contrasty substance 20. As may be seen in FIGS. 2 and 3, there is a bore 26 in the head 24 serving to receive a pin 32 with accurate fit.

The substance 20 in the head 24 on the one hand, for example, allows a computer tomogram to be taken and, upon exchange of the marker, a roentgenogram. The fixture 10 (FIG. 1) used in each case remains unaltered. Alterations are not needed because the material of which the fixture 10 is made does not disturb either computer tomography or X-ray examination.

The embodiment illustrated in FIG. 3 differs from the one described above with reference to FIG. 2 in that the head 24 is formed with a channel 30 through which a contrasty substance can be injected into a cavity 28. The substance used may be a contrast medium containing gadolinium. Following the injection, the channel 30 is closed by suitable means.

The channel 30 also may be of such design that the surface tension of the contrast medium (being a liquid) will prevent it from leaking out.

The markers illustrated in FIGS. 2 and 3 have the same dimensions and are adapted to the dimensions of the fixture 10 so that they can be slipped selectively into the fixture 10, while containing different contrasty substances.

Figure 4:
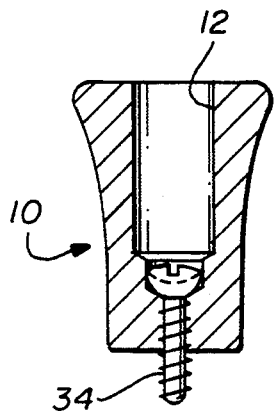
FIG. 4 shows another embodiment of a fixture.

FIG. 4 illustrates a fixture 10 for implantation into the body. Again the recess 12 serves to receive a marker (for instance, of the type shown in FIGS. 2 and 3), while a screw 34 helps to secure the fixture 10 to a bone, for example a skull bone. As was the case with the embodiments described above, the fixture is made of a plastic material which is compatible with the body, whereas the screw 34 is a metallic bone screw.

Figure 5:
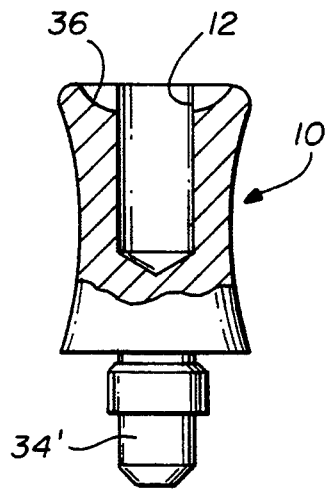
FIG. 5 shows yet another embodiment of a fixture.
Figure 6:
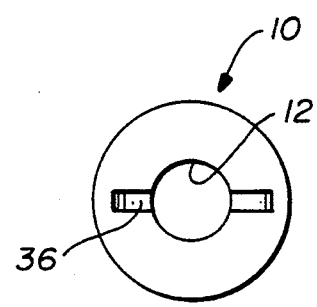
FIG. 6 is a top plan view of a fixture according to FIG. 5.

Another embodiment of a fixture 10 is presented in FIGS. 5 and 6. This fixture 10 can be used together with a bone screw already implanted. The fixture 10 is mounted by screwing a limb 34' thereof onto the already fastened bone screw. The proximal end of the fixture 10 includes a slot 36 at which to apply the screwdriver.

Figure 8:
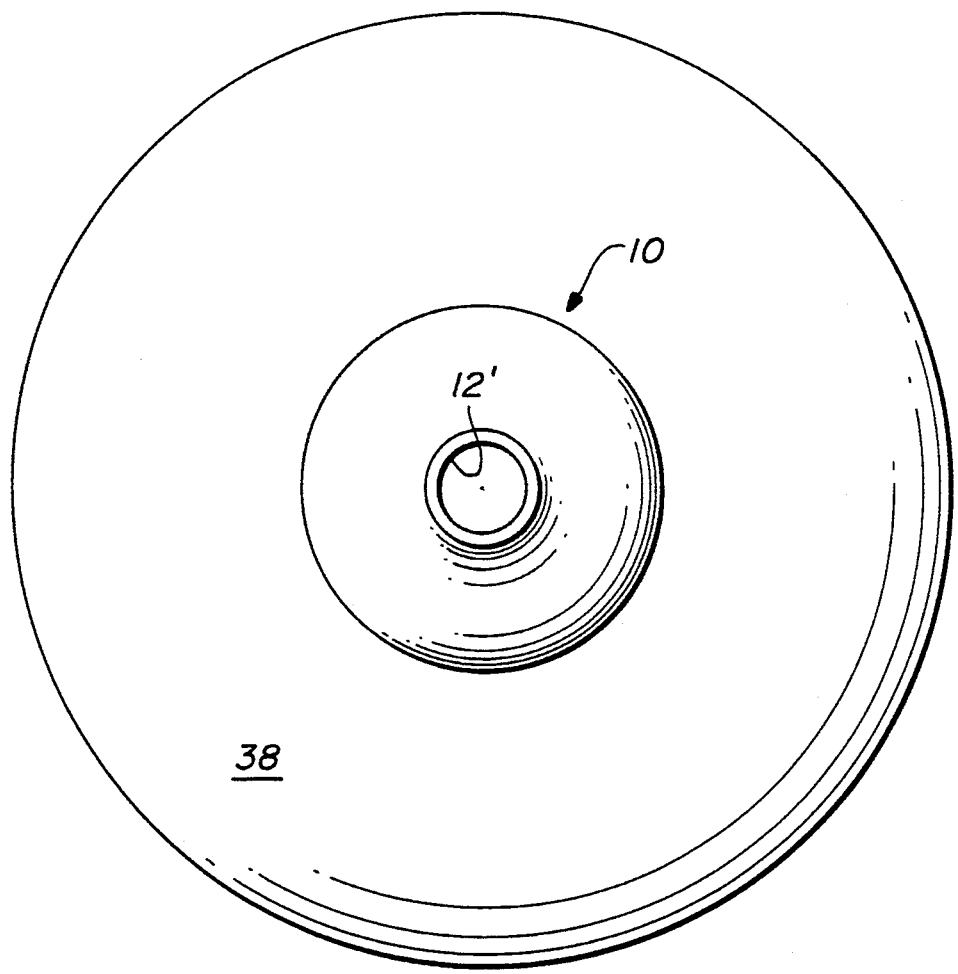
FIG. 8 is a top plan view of a fixture according to FIG. 7.
Figure 7:
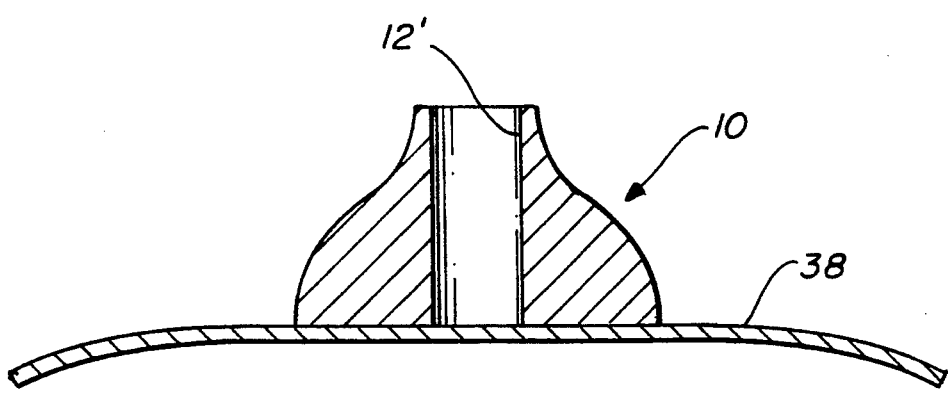
FIG. 7 shows another embodiment of a fixture having a base plate.

FIGS. 7 and 8 show another embodiment of a fixture, this being one for adhering to a surface of the body. The fixture 10 comprises a body approximately of bell shape and formed with a recess 12' into which a limb 22 according to FIGS. 2 and 3 can be inserted in a manner analogous to the embodiments described above with reference to FIGS. 1, 4, and 5. A plate 38 serves to attach the fixture 10, for example, to the skin. The plate 38 is held in place by a suitable adhesive.

FIG. 8 is a top plan view of the embodiment described with reference to FIG. 7.

Figure 10:
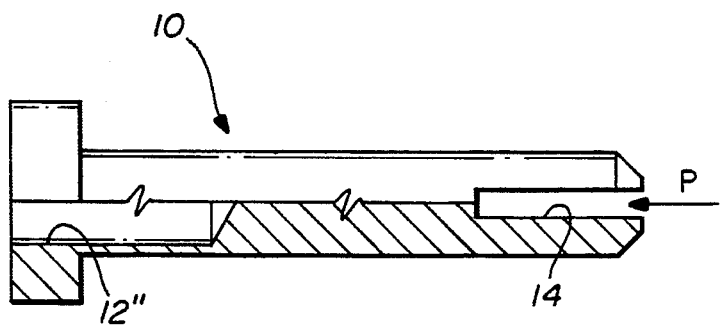
FIG. 10 shows an embodiment of a fixture adapted to be fastened to a stereotaxic system.
Figure 9:
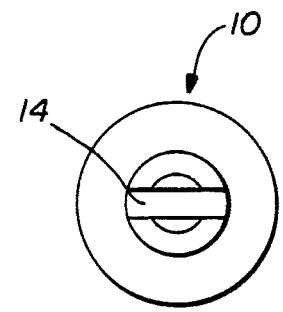
FIG. 9 is a view of the fixture shown in FIG. 10, as seen in the direction of arrow P.

FIGS. 9 and 10 illustrate a fixture 10 adapted to be fastened to a stereotaxic system. To this end, the fixture 10 is formed like a pin (FIG. 10). This pin can be pushed into a bore provided in the stereotaxic system until its greater diameter portion comes to abut on it. Subsequently, a marker 18, e.g. of the type shown in FIGS. 2 and 3, can be inserted in the recess 12". FIG. 9 is a presentation of the pin as seen in the direction of arrow P in FIG. 10. The fixture 10 according to FIG. 10 is embodied by the pin. As will be seen, there is a slit 14 which produces clamping effect in a bore of the stereotaxic system.

Figure 11:
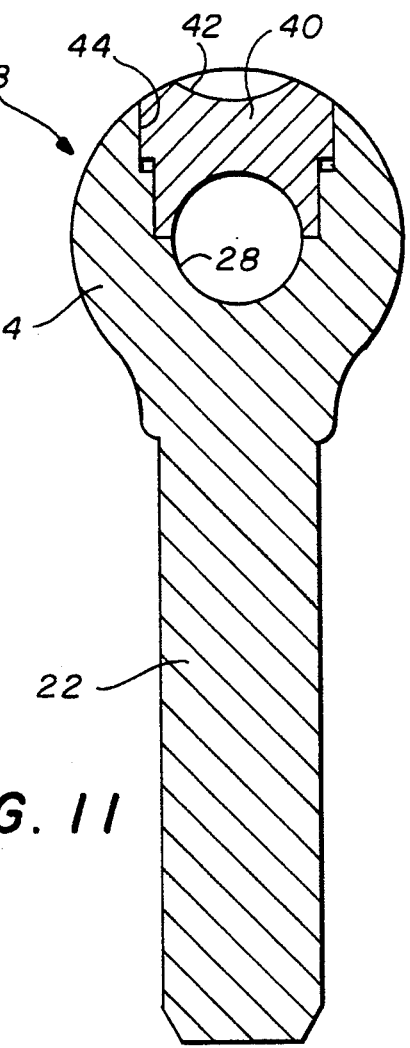
FIG. 11 shows another embodiment of a marker which can be used, for example, with one of the fixtures mentioned above.

FIG. 11 illustrates another embodiment of a marker 18, i.e. a modification of the marker described with reference to FIGS. 2 and 3. The limb 22 again serves for fastening the marker in a fixture, for instance of the type shown in FIGS. 1 and 4 to 10. The head 24 of the marker 18 shown in FIG. 11 comprises a cap 40 which, when removed, allows access to the cavity 28 into which the contrasty substance can be filled. The cap 40, being designed like a threaded-type closure, has a hemispherical recess at its bottom supplementing a recess of complementary hemispherical shape in the head 24 so as to form a full sphere. FIG. 11 also shows the thread 44 by which the cap 40 is screwed into the head 24 as well as a slot 42 for engagement of a screwdriver.

Both the head 24 and the limb 22 as well as the cap 40 can be made of polytetrafluoroethylene.

Figure 14:
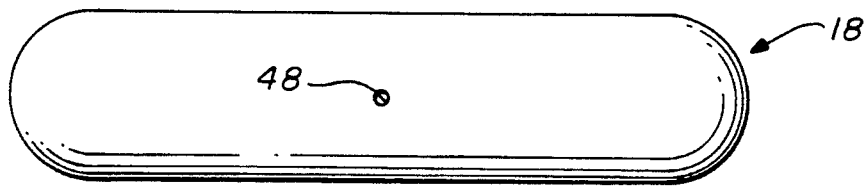
FIG. 14 is a top plan view of the marker shown in FIG. 12.
Figure 12:
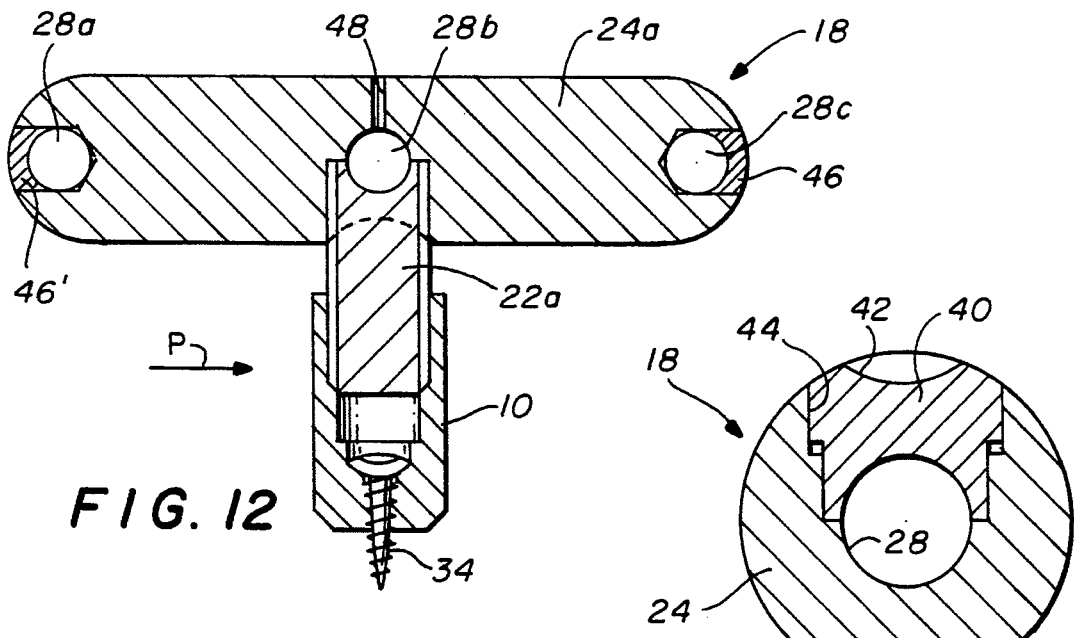
FIG. 12 shows an embodiment of a marker into which different contrast media can be introduced.
Figure 13:
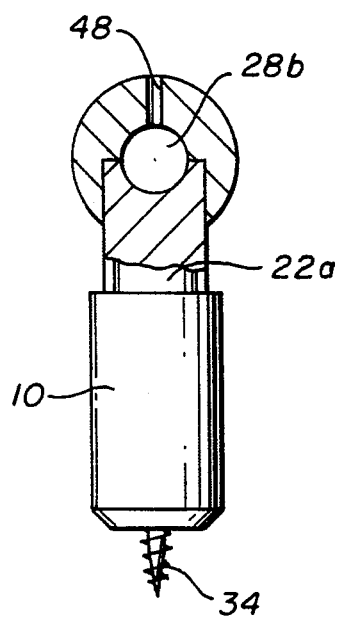
FIG. 13 is a view of the marker according to FIG. 12, as seen in the direction of arrow P.

Another embodiment of a marker 18 is presented in FIGS. 12, 13, and 14. Once more a limb 22a is inserted into a fixture 10 (e.g. according to FIGS. 1, 4–10). This is illustrated in FIGS. 12 and 13. The marker 18 comprises an arm-like transverse body 24a which extends transversely of the limb 22a and includes more than one cavity to receive contrasty substances, namely cavities 28a, 28b, and 28c. These cavities may contain different substances at the same time. A channel 48 links the cavity 28b with the outside. The cavities 28a and 28c can be sealed from the outside by a plug 46, 46' each. The plugs, for example, can be glued in place. The geometric center of the two outer cavities 28a, 28c coincides with the center of the middle cavity 28b.

Figure 15:
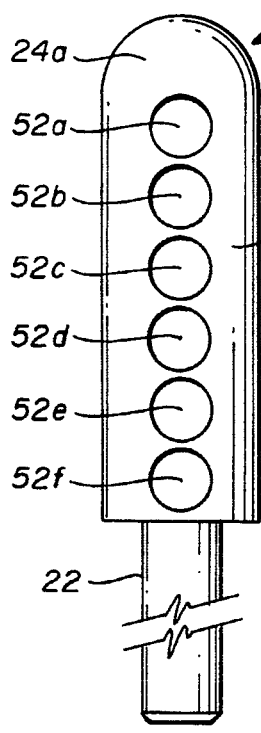
FIG. 15 shows another embodiment of a marker, including a plurality of receptacles for different contrast media.
Figure 16:
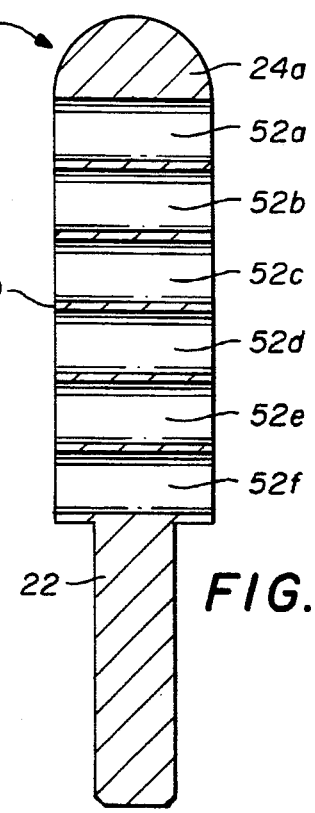
FIG. 16 is an axial sectional elevation of a marker as shown in FIG. 15.
Figure 17:
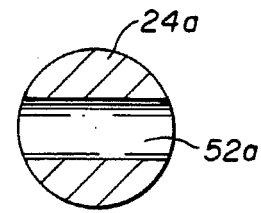
FIG. 17 is a sectional elevation perpendicular to the longitudinal axis of a marker according to FIG. 15.
Figure 18:
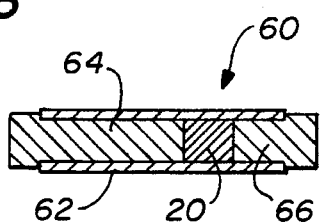
FIGS. 18–20 show different embodiments of inserts for use with markers such as shown in FIGS. 15, 21 and 22.
Figure 19:
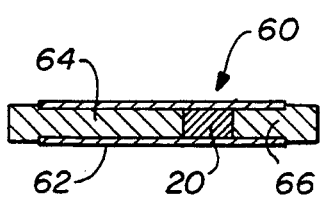
Figure 20:
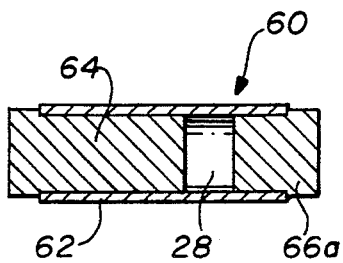

FIGS. 15 to 17 show another embodiment of a marker 18 adapted to receive different, exchangeable constrast media at the same time. The head 24a of the marker 18 is formed with a plurality of cylindrical, through cavities 52a to 52d into which inserts can be slid, as shown in FIGS. 18 to 20, each containing the particular constrast substance. Thus, inserts 60 as shown in FIGS. 18 to 20 can be inserted into the cavities 52a to 52d. This means that different contrast media can be used at selectable spacings from one another. The centers of the individual slip-in inserts 60 containing the contrast substance lie on the same axis, this being the longitudinal axis of the marker 18 and its limb 22 in the embodiment illustrated. In this manner, specifically the geometric centers of two outer markers can coincide with the center of a centrally located marker.

FIGS. 18, 19, and 20 show inserts 60 for use, for instance, with a marker 18 according to FIGS. 15 to 17.

An insert 60 comprises a hose 62 made, for instance, of polytetrafluoroethylene. Rods 64 and 66, respectively, can be pushed from either end into the hose 62 so that a cavity remains in the middle of the hose to be filled with a contrasty substance (providing contrast in the particular imaging process applied). In the case of the embodiment according to FIG. 20, the cavity 28 at first is not filled. The rods 64 and 66a are designed in such a way that they can be pulled off the hose 62 so that the user can fill the cavity 28 optionally with the desired contrast medium.

Figure 21:
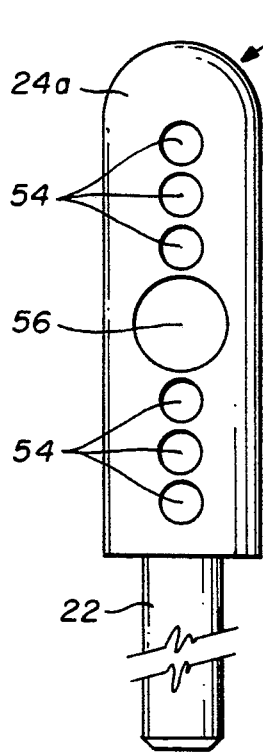
FIG. 21 shows another embodiment of a marker, presenting a modification of the embodiment illustrated in FIG. 15.
Figure 22:
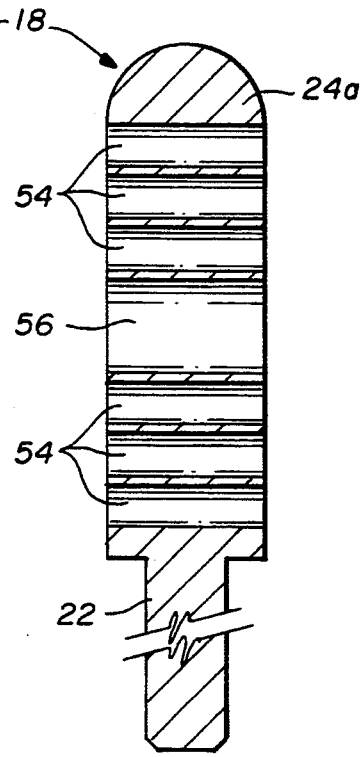
FIG. 22 is an axial sectional elevation of a marker as shown in FIG. 21.

Another embodiment of a marker 18, similar to the one illustrated in FIGS. 15 and 16, is presented in FIGS. 21 and 22. In this case, however, inserts of different sizes are insertable in individual cavities. Inserts having a smaller diameter can be placed in the cavities 54, while an insert of greater diameter can be received by cavity 56. In this manner, too, the geometric centers of two outer markers can be made to coincide with the center of the centrally positioned marker.

In the above description of preferred embodiments, structural elements which are similar or fulfill the same or similar functions have been designated by like reference numerals, modifications having been marked by a single or double prime accent or small letters.

Suitable material for the fixtures, in particular the limbs and the body of the fixtures according to FIGS. 1, 4, 5, 7, etc. especially is polysulfon (PSU). Polysulfon is suitable for implants, can be sterilized, and is transparent so that it permits optical association of the filler material to be made.

Suitable material for a marker 18, for example as shown in FIGS. 2 and 3, especially is polysulfon or metal, such as titanium.

Polysulfon likewise is a suitable material for the fixture shown in FIG. 7, while the base plate 38 can be a conventional electrode adhesive ring.

A fixture such as shown in FIGS. 9 and 10, for example, can be made of a polyamide, a polyamide-imide or a similar resin.

A marker of the type presented in FIG. 11, for example, can be made of polytetrafluoroethylene (Teflon, PTFE) or polysulfon (PSU), or any other plastic material suitable for implantation.

It follows from the above description of preferred embodiments that the markers (especially marker 18 according to FIGS. 2 and 3) are characterized by spherical symmetry so that they provide the same image in every viewing direction. That makes it possible to precisely determine a position in sectional or projection images as well as in optical processes.

Due to their triple or multiple symmetry, the markers can be imaged at the same time in various imaging processes, which allows various contrast media to be used simultaneously (embodiments according to FIGS. 12 and 15 to 22). Also, different contrast substances can be used at the same time in one and the same marker.

In particular, a contrast medium can be used which provides good imaging both in nuclear spin resonance tomography (NMR) and in computed tomography (CT).

The embodiments shown, further, are characterized (FIGS. 2, 3) by the fact that the center of a spherical contrast medium coincides with a clearly defined, optically visible center of the marker 18 which, specifically, is of spherical shape.

What is claimed is:

1. A device for marking body sites for imaging medical examination procedures comprising:
   fixtures made of a material that does not disturb the imaging with at least two different imaging examination procedures and adapted to be fastened either to the body or to a stereotaxic means;
   markers releasably fastened to the fixtures and including a substance which is contrasty in imaging; and
   at least two different markers to be attached to a fixture, each in a predetermined position and each having a contrasty substance for different imaging examination procedures.

2. A device as in claim 1 wherein said fixtures adapted to be fastened to a stereotaxic means further includes:
   an elongated structure having an upper portion and a lower portion, said upper portion having a larger diameter than said lower portion; and
   said lower portion including clamping means for fastening said fixtures to said stereotaxic means.

3. A device as in claim 2 wherein said clamping means of said lower portion of said fixture engages a bore in said stereotaxic means and further comprises:
   first and second spreader wings separated by a slot forming said lower portion, said lower portion adapted to be fastened to said stereotaxic means by insertion of said lower portion in said bore provided in said stereotaxic means until the larger diameter of said upper portion abuts said bore; and said spreader wings providing said clamping effect in said bore in said stereotaxic means.

4. A device as in claim 3 wherein said fixture further includes an elongated recess in said elongated portion of said fixture for receiving one of said markers.

5. A device as in claim 1 wherein said fixture adapted to be fastened to the body further includes:

an elongated structure having a first orifice of a first diameter extending partially therein for receiving said marker; and a second orifice of smaller diameter extending from the termination of said first orifice through the remainder of said elongated structure, said second orifice enabling a bone screw to be inserted therein for attaching said fixture to said body.

6. A device as in claim 1 wherein said fixture adapted to be fastened to the body further comprises:

an elongated structure having an upper portion and a lower portion;

said upper portion including an orifice therein for releasably receiving said marker;

said lower portion having a threaded orifice therein for attachment to a bone screw previously attached to the body; and a slot in said upper portion for enabling the use of a screwdriver to attach said fixture to said bone screw.

7. A device as in claim 1 wherein said fixture adapted to be fastened to said body further comprises:

a substantially bell-shaped body having an orifice therein for receiving said fixture; and a plate larger than said bell-shaped body and attached to said bell-shaped body for attachment to the skin of a body.

8. A device as in claim 7 wherein said plate is adhesively attached to the skin of said body.

9. A device as in claim 1 further including a bore in said fixture for receiving said marker.

10. A device as in claim 9 wherein said marker includes: an upper portion and a lower portion;

said lower portion being elongated for insertion in said bore in said fixture; and said upper portion including a cavity for receiving a contrasty substance for said imaging medical examination procedure.

11. A device as in claim 10 further including an orifice in said upper portion extending into said cavity to enable said contrasty substance to be inserted therein.

12. A device as in claim 11 wherein said orifice extending into said cavity is designed such that surface tension of said contrasty substance will prevent said contrasty substance from leaking out of said cavity.

13. A device as in claim 11 further including an elongated slot extending partially into said lower portion of said marker to form first and second spaced spreader wings to create a clamping effect when inserted in said bore of said fixture.

14. A device as in claim 10 wherein said marker further includes:

a cap removably attached to said upper portion of said marker such that, when removed, said contrasty substance can be placed in said cavity; and when said cavity is filled with said contrasty substance, said cap may be replaced to seal said contrasty substance in said cavity.

15. A device as in claim 14 wherein:

said cap is threadedly attached to said marker upper portion;

said cavity is spherical in shape; and a hemispherical recess is formed in said cap and said marker upper portion to complement each other and form said spherical cavity when said cap is threadedly attached to said marker upper portion.

16. A device as in claim 10 wherein said upper portion of said marker includes:

an arm-like transverse body extending transversely of said lower portion;

a plurality of spaced cavities in said transverse body, each cavity receiving contrasty substances; and access means for each cavity in said transverse body for inserting said contrasty substance.

17. A device as in claim 10 wherein said upper portion of said marker includes:

a vertically extending portion integrally formed with said lower portion;

a plurality of spaced-through cavities extending transversely through said vertically extending portion; and inserts slidably mounted in at least one of said cavities, each insert having a hollow portion containing a particular contrasty substance such that different contrast media can be used at selected spacings from each other.

18. A device as in claim 17 wherein:

the longitudinal centers of said cavities lie vertically along the longitudinal axis of said vertically extending portion of said marker; and the longitudinal centers of said inserts, when in said cavities, all lie vertically along the same axis.

19. A device as in claim 18 wherein said inserts comprise:

an elongated cylindrical hollow body; and first and second hollow rods partially and removably inserted in corresponding ends of said hollow cylindrical body so as to form a cavity between said first and second rods in which said contrasty substance may be received.

20. A device as in claim 17 wherein:

said transversely extending cavities in said upper portion are of different sizes; and said inserts are of corresponding different sizes for insertion in corresponding size cavities.

21. A device as in claim 10 wherein said upper portion of said marker is formed as a sphere to provide spherical symmetry and enable the same viewing image to be obtained in every direction.

22. A device for marking body sites for imaging medical examination procedures comprising:

fixtures adapted to be releasably fastened either to said body or to a stereotaxic means attached to said body;

markers containing a substance which is contrasty in the imaging, said markers being adapted to be releasably fastened to said fixtures; and said fixtures being made of a material that does not disturb the imaging with at least two different imaging examination procedures.

\* \* \* \* \*

Adverse Decision In Interference

Patent No. 5,394,457, Karl Leibinger, Franz Leibinger, Stephan Felber, Clemens Plangger, DEVICE FOR MARKING BODY SITES FOR MEDICAL EXAMINATIONS, Interference No. 103,657, final judgment adverse to the patentee rendered December 5, 2000, as to claims 1-22.
*(Official Gazette April 10, 2001)*